(12) United States Patent
Mick et al.

(10) Patent No.: US 9,099,209 B2
(45) Date of Patent: Aug. 4, 2015

(54) BLADDER AND/OR RECTUM EXTENDER WITH EXCHANGEABLE AND/OR SLIDEABLE TUNGSTEN SHIELD

(75) Inventors: Felix W. Mick, Bronxville, NY (US); Paul DaSilva, Flushing, NY (US)

(73) Assignee: MICK RADIO-NUCLEAR INSTRUMENTS, INC., Mt. Vernon, NY (US)

( * ) Notice: Subject to any disclaimer, the term of this patent is extended or adjusted under 35 U.S.C. 154(b) by 64 days.

(21) Appl. No.: 13/540,193

(22) Filed: Jul. 2, 2012

(65) Prior Publication Data

US 2013/0023717 A1    Jan. 24, 2013

Related U.S. Application Data

(60) Provisional application No. 61/504,064, filed on Jul. 1, 2011, provisional application No. 61/512,387, filed on Jul. 27, 2011.

(51) Int. Cl.
*G21F 3/00* (2006.01)
*A61M 36/00* (2006.01)
*A61N 5/10* (2006.01)
*A61B 19/00* (2006.01)

(52) U.S. Cl.
CPC ................ *G21F 3/00* (2013.01); *A61N 5/1016* (2013.01); *A61N 5/1049* (2013.01); *A61B 2019/4045* (2013.01); *A61B 2019/4081* (2013.01); *A61N 2005/1094* (2013.01)

(58) Field of Classification Search
CPC .................. G21F 3/00; A61N 5/1016; A61N 2005/1094; A61N 5/1049; A61B 2019/4045; A61B 2019/4081
USPC ............................ 600/1–7; 250/506.1, 496.1; 128/897–899
See application file for complete search history.

(56) References Cited

U.S. PATENT DOCUMENTS

| 4,292,960 | A |   | 10/1981 | Paglione |
|---|---|---|---|---|
| 4,554,909 | A | * | 11/1985 | Pino y Torres .................... 600/6 |
| 5,562,594 | A | * | 10/1996 | Weeks ............... 600/3 |
| 6,390,968 | B1 | * | 5/2002 | Harmon ............................ 600/6 |
| 7,556,596 | B2 |   | 7/2009 | Mourtada et al. |
| 2006/0235260 | A1 |   | 10/2006 | Mourtada et al. |
| 2008/0064916 | A1 |   | 3/2008 | Mick |

FOREIGN PATENT DOCUMENTS

WO    2011/011731    1/2011

OTHER PUBLICATIONS

International Search Report and Written Opinion, dated Oct. 1, 2012, issued in corresponding International Application No. PCT/US2012/045267.

* cited by examiner

*Primary Examiner* — Christine H Matthews
*Assistant Examiner* — Sunita Reddy
(74) *Attorney, Agent, or Firm* — Kenyon & Kenyon LLP

(57) ABSTRACT

A shielding device includes two elongated, parallel tubes joined at a distal portion, and a shield at least one of removably and slidably situated at the distal portion. An assembly includes an applicator configured for a treatment site, an assembly block attached to the applicator, at least one rotary unit configured to be rotatably received in the assembly block, and at least one shielding device that is configured to be movably received in a respective rotary unit. A method of using the shielding device with an applicator includes inserting the distal portion of the shielding device to a treatment site, and adjusting a position of the distal portion relative to a distal end of the applicator.

18 Claims, 17 Drawing Sheets

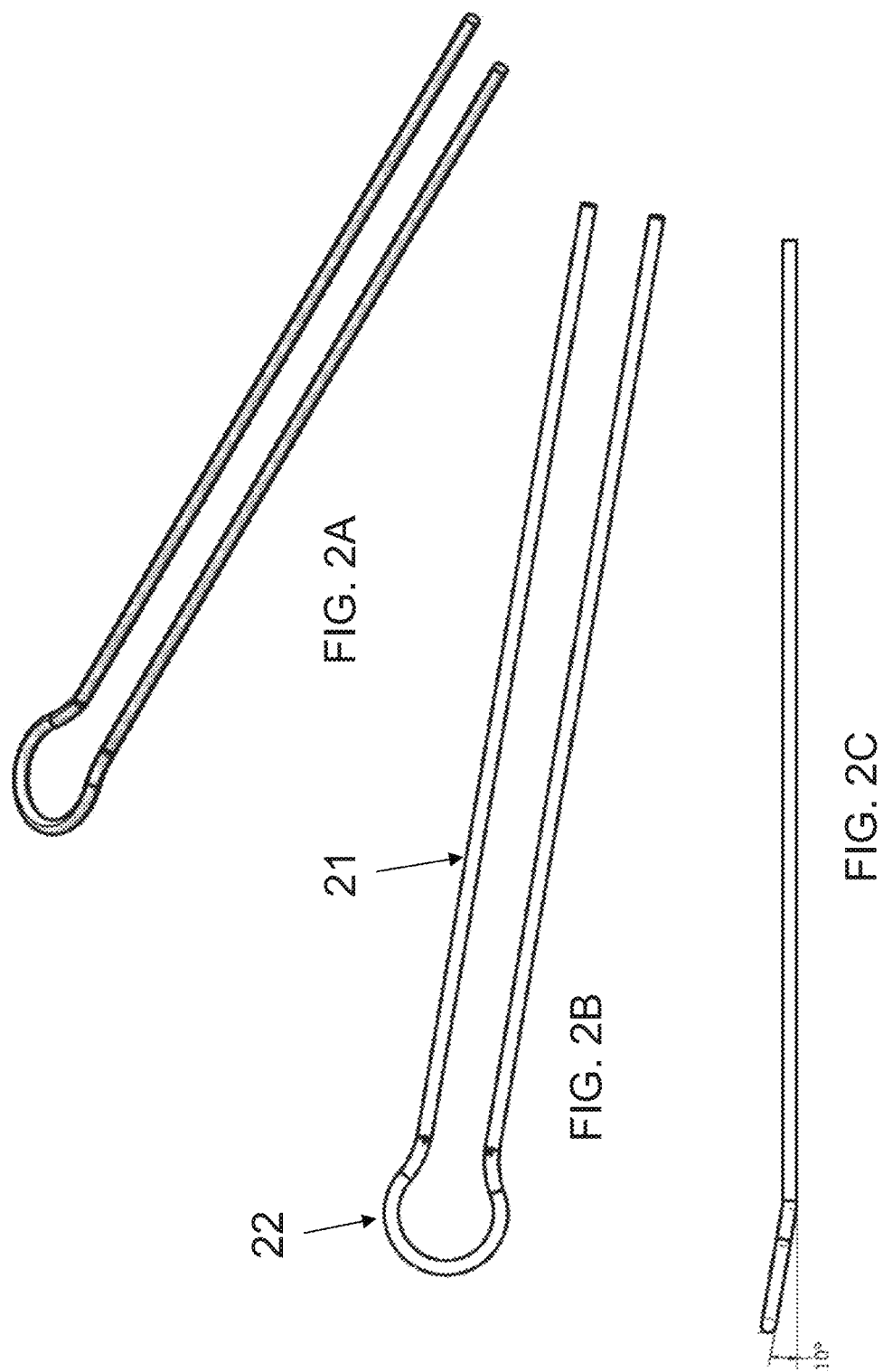

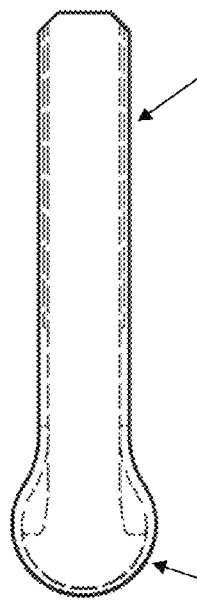
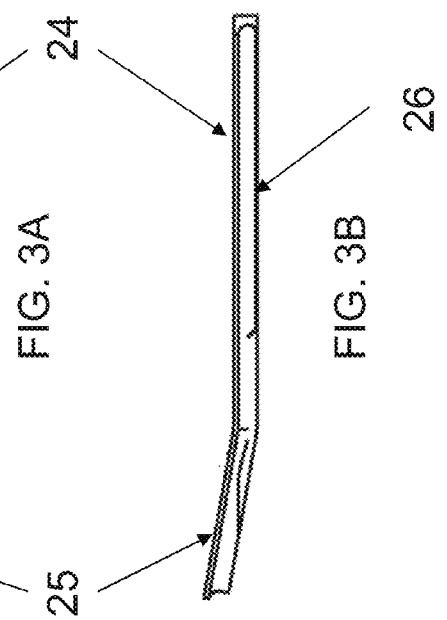
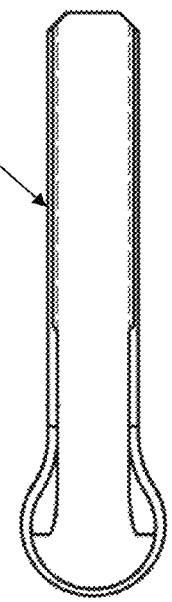
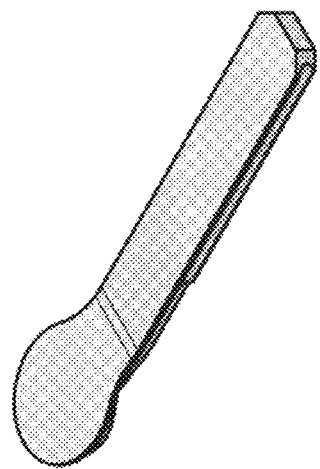
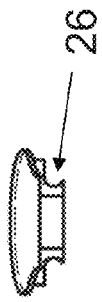
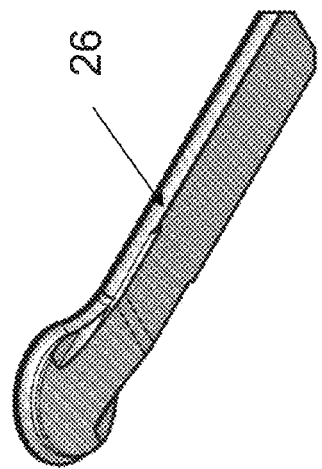

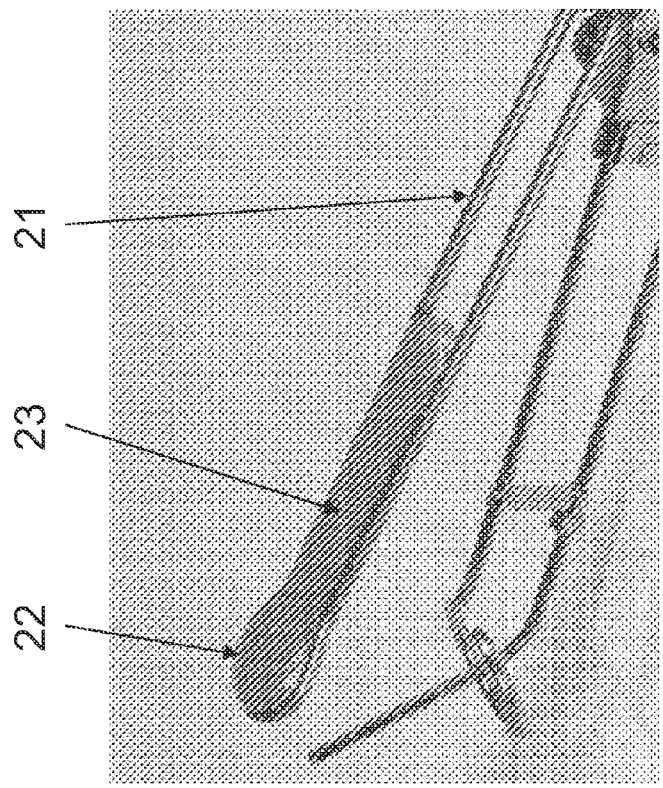
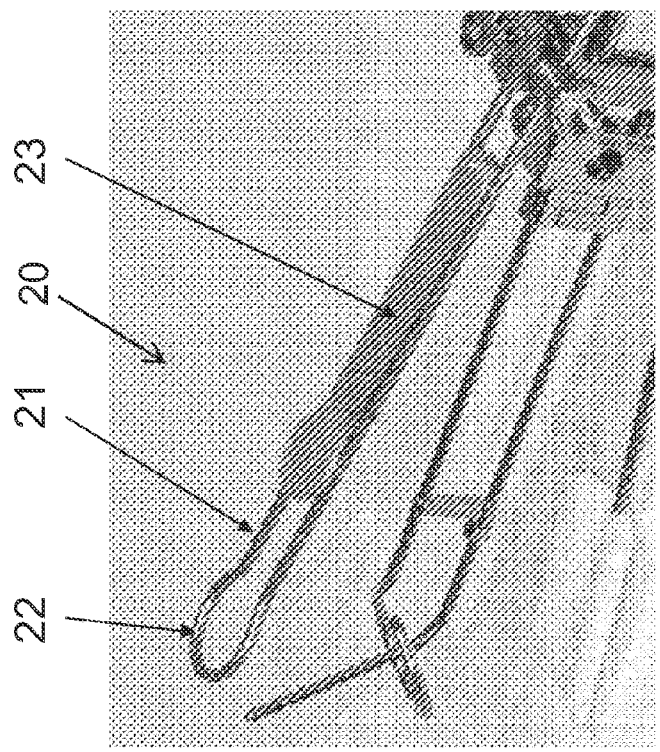
FIG. 4A
FIG. 4B

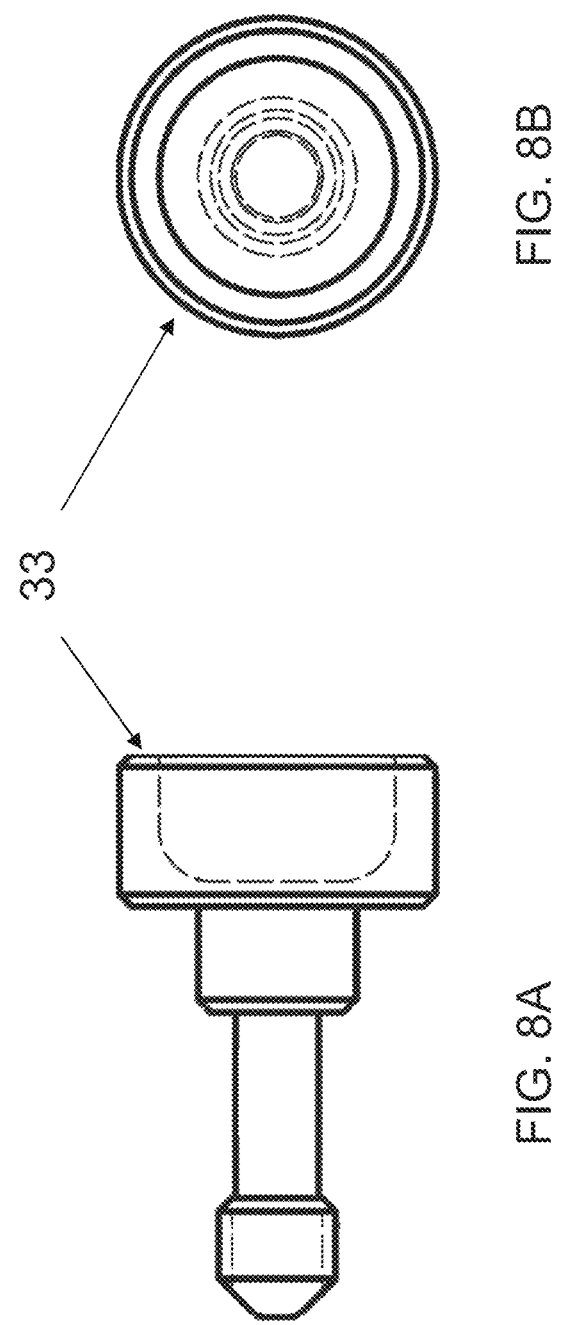

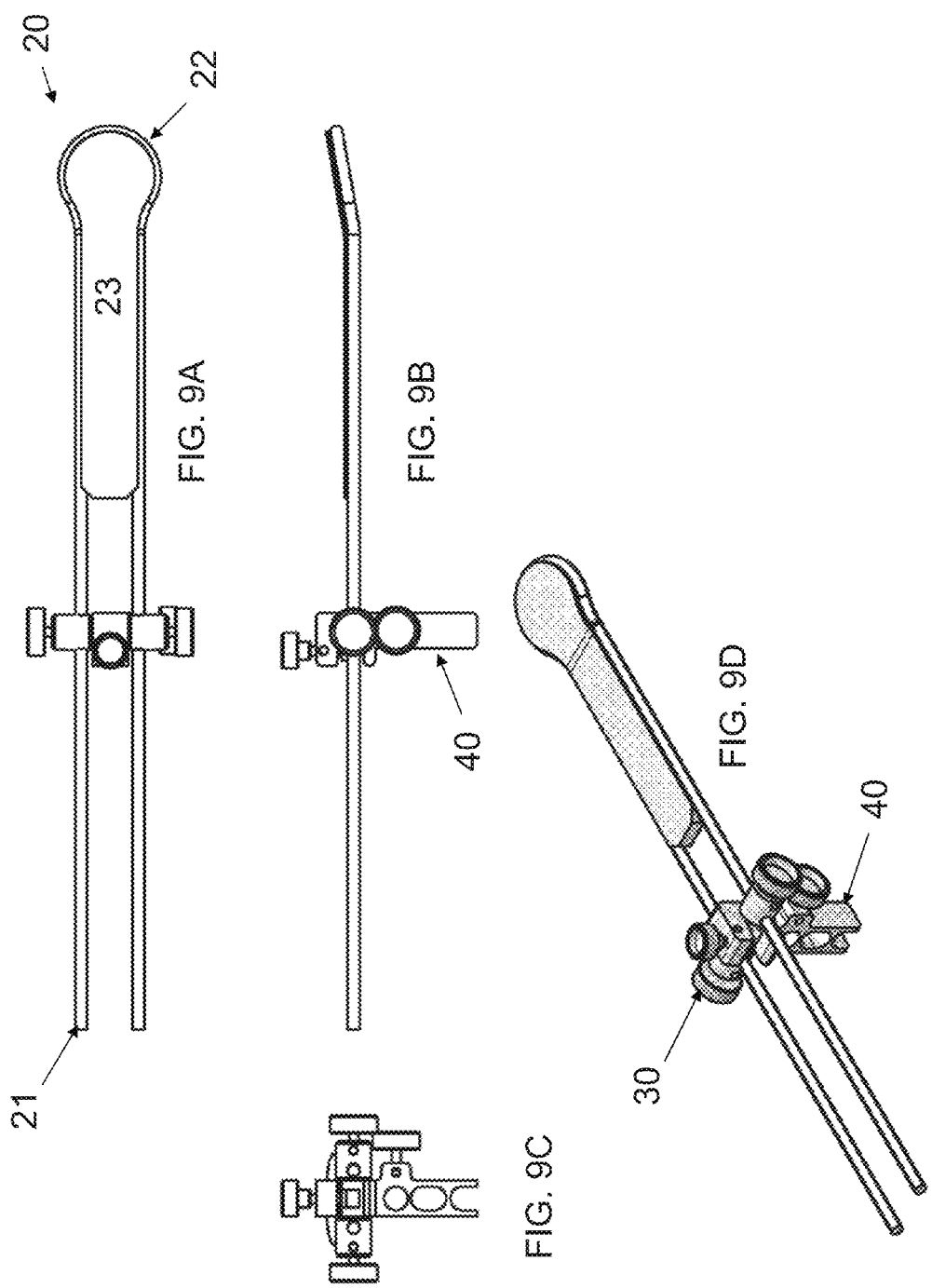

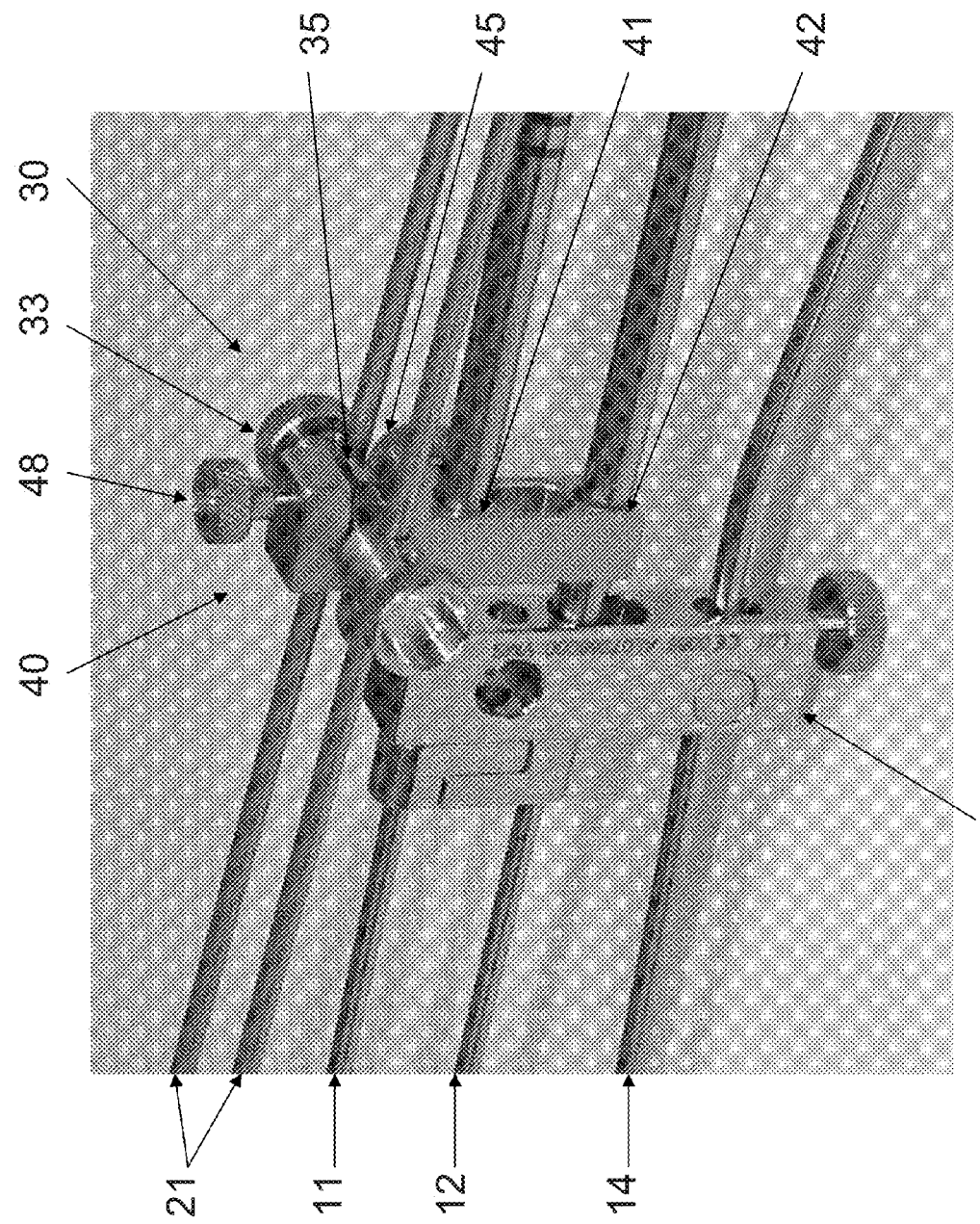

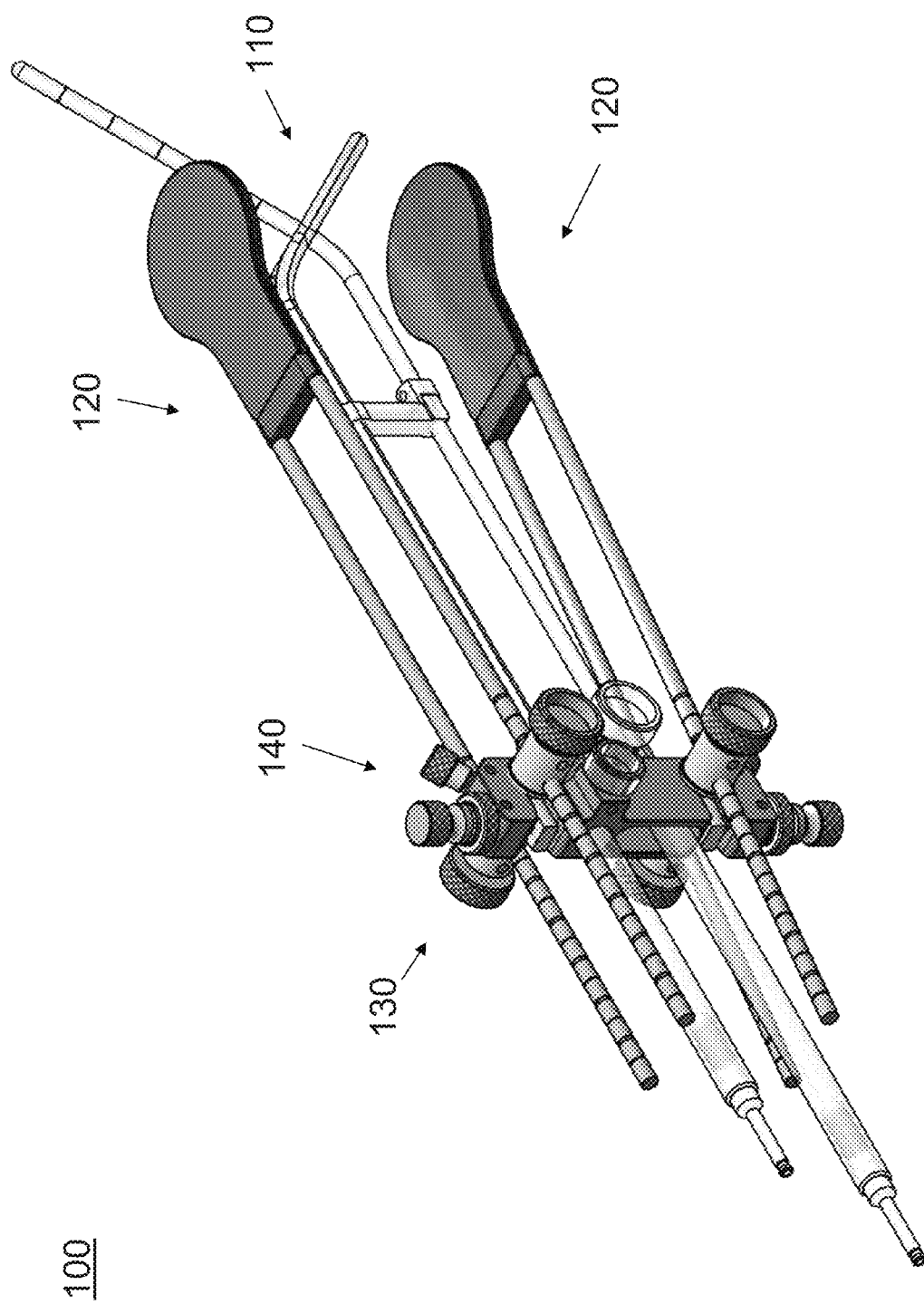

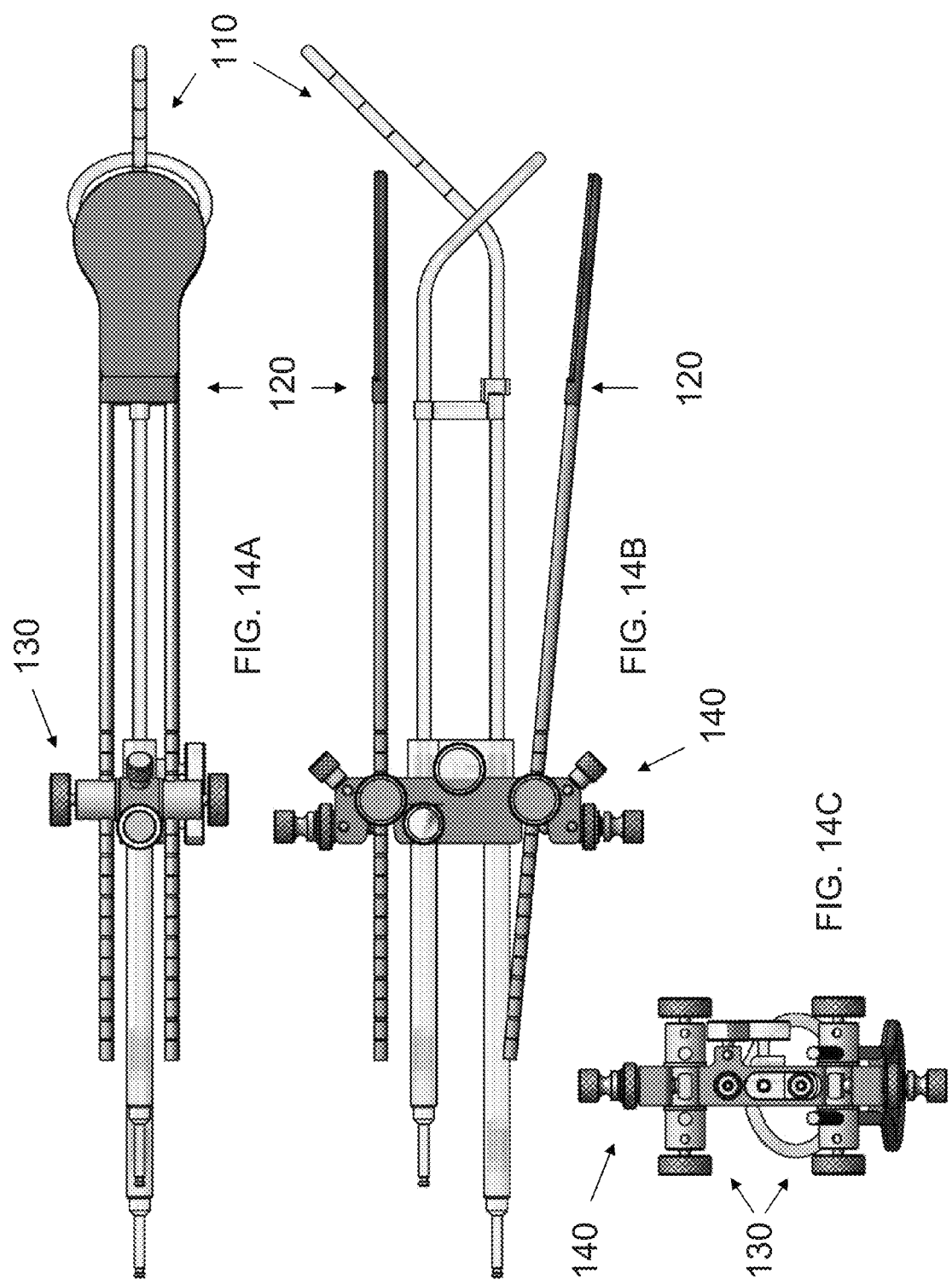

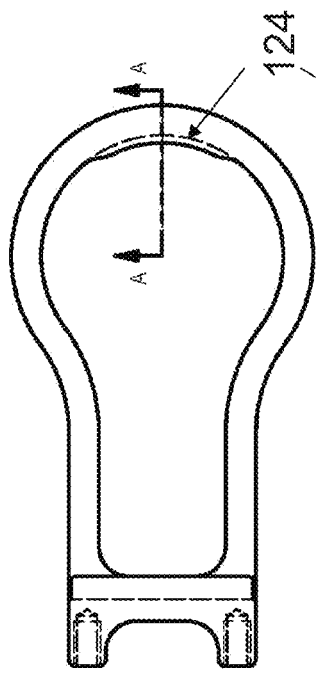
FIG. 15C
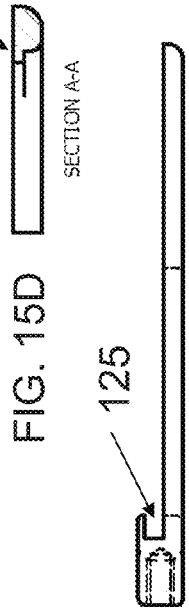
FIG. 15D
FIG. 15E
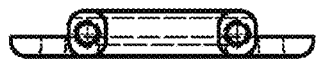
FIG. 15B
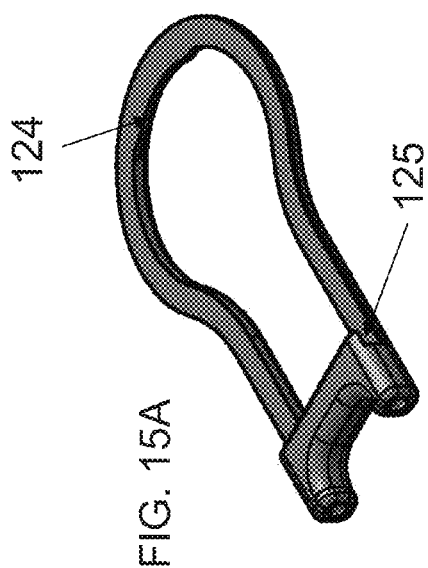
FIG. 15A

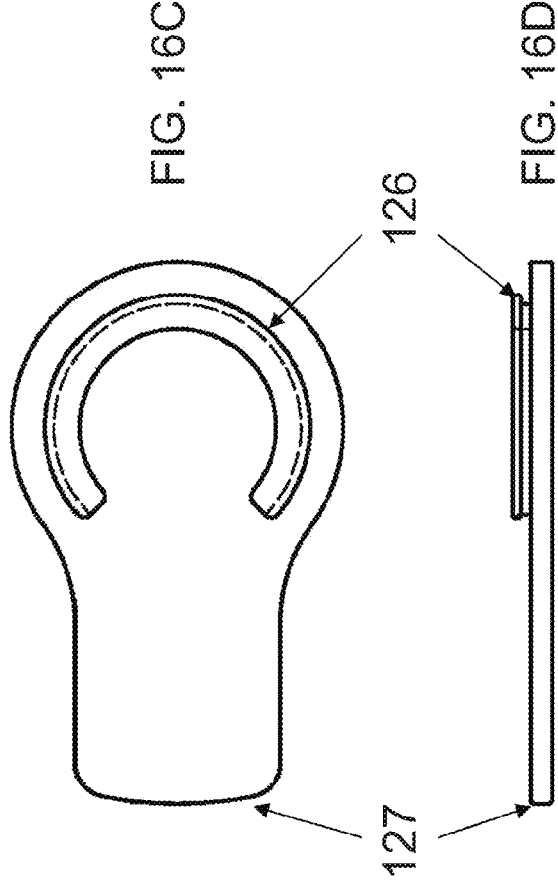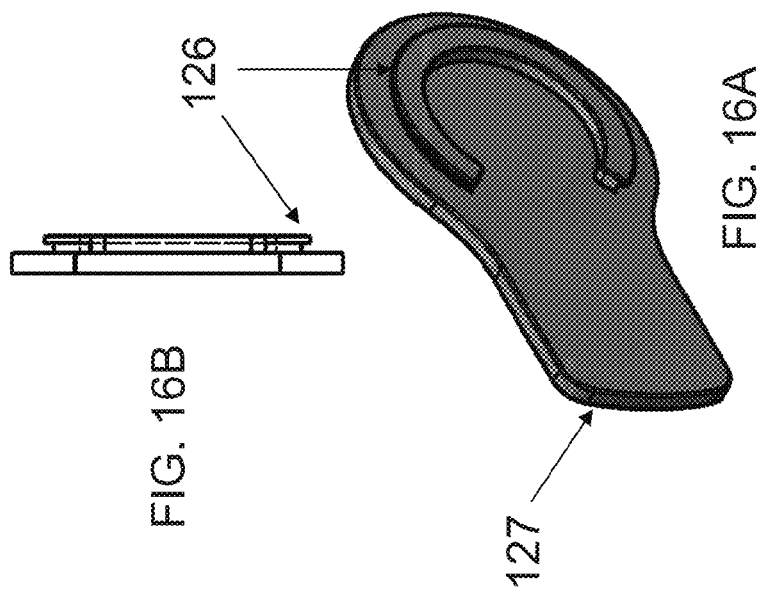

BLADDER AND/OR RECTUM EXTENDER WITH EXCHANGEABLE AND/OR SLIDEABLE TUNGSTEN SHIELD

CROSS-REFERENCE TO RELATED APPLICATION

The present application claims the benefit of U.S. Provisional Patent Application No. 61/504,064, filed on Jul. 1, 2011, which is expressly incorporated herein in its entirety by reference thereto.

FIELD OF THE INVENTION

The present invention relates generally to a shielding device for use during radiation treatment, an assembly comprising the shielding device, and a method of using the shielding device.

BACKGROUND INFORMATION

During treatment of cancer, for example, using either external beam radiation and/or high dose rate brachytherapy, other healthy organs may be subjected to undesirable radiation due to their anatomical location with respect to a treatment site. For example, during treatment of cancer of a cervix, a patient's rectum and/or bladder may be subjected to undesirable radiation due to their proximity to the cervix.

Medical practitioners have long been plagued by the undesirable exposure to radiation of healthy organs while delivering a prescribed dose of radiation to a treatment site, such as a patient's cervix. Therefore, there is believed to be a need to prevent such undesirable exposure to radiation of healthy organs while providing the prescribed dose of radiation to the treatment site.

SUMMARY

Example embodiments of the present invention prevent undesirable exposure to radiation of healthy organs, for example, the rectum and/or bladder when treating a patient's cervix, by physically lifting and/or pushing the rectum and/or bladder away from the treatment site as far as anatomically possible using a shielding device. For example, the bladder may be lifted up from its sagging position and pushed anterior and away from the cervix.

In addition to the physical displacement of healthy organs, the shielding device may include an exchangeable and/or moveable shield, for example, made of tungsten, to further reduce exposure to radiation of healthy organs. The shield may be removed, exchanged, and/or moved as required in order to facilitate imaging, treatment planning, and/or actual treatment.

In accordance with example embodiments of the present invention, a shielding device may include two elongated, parallel tubes joined at a distal portion, and a shield at least one of removably and slidably situated at the distal portion. The distal portion may be angled up to about 10 degrees relative to a plane defined by the tubes, and may include at least one of a U-shaped and a circular portion. The tubes may include markings configured to indicate a longitudinal position, and may be made of medical grade titanium.

The shield may be made of tungsten and/or brass, and may be between about 2 mm to about 5 mm thick. The shield may be configured to extend at least a length of the distal portion along a longitudinal axis of the tubes. In addition, the shield may include grooves for attachment to the tubes.

Further, the distal portion may include a separate shield retainer attached to distal ends of the tubes. The shield retainer may include a retaining lip and a key slot configured to retain the shield, and the shield may include a retaining ring and a key portion configured to be received by the retaining lip and the key slot, respectively.

The shielding device may be configured to be attached to an applicator via a rotary unit and an assembly block. The shielding device may be movable within the rotary unit and the assembly block at least one of longitudinally along a longitudinal axis of the tubes and rotationally towards or away from a distal end of the applicator. The shielding device may be configured to at least one of move and shield one of a bladder and a rectum during treatment of a patient's cervix.

In accordance with example embodiments of the present invention, an assembly may include an applicator configured for a treatment site, an assembly block attached to the applicator, at least one rotary unit configured to be rotatably received in the assembly block, and at least one shielding device, each respective shielding device including two elongated, parallel tubes joined at a distal portion, and a shield at least one of removably and slidably situated at the distal portion, in which the tubes of a respective shielding device are configured to be movably received in a respective rotary unit.

The assembly, except for the shield, may be made of medical grade titanium. The assembly block may be attached to the applicator via an applicator lock screw, and may include a circular hole, an elongated hole, and/or a U-shaped hole for receiving the applicator.

The rotary unit may be rotatably retained in the assembly block via a capture screw. The tubes may be secured in the rotary unit via shield depth lock screws. The rotary unit may include a pivot pin, and the assembly block may include at least one angle adjustment screw configured to interact with the pivot pin, the pivot pin and the angle adjustment screw configured to set a rotational position of the rotary unit when received in the assembly block. The pivot pin may be triangular and/or rectangular. The at least one angle adjustment screw may include an angle location lock nut configured to reproducibly set the rotational position.

The shielding device may be configured to move and/or shield a bladder and/or a rectum during treatment of a patient's cervix.

In accordance with example embodiments of the present invention, a method of using a shielding device with an applicator may include inserting the distal portion of the shielding device to a treatment site, and adjusting a position of the distal portion relative to a distal end of the applicator. The adjusting may include setting a longitudinal depth of insertion of the distal portion, and setting a rotational position of the distal portion relative to the distal end of the applicator. The method may further include after the adjusting, removing the distal portion of the shielding device from the treatment site, and reproducibly reinserting the distal portion to a previously adjusted position. The method may further include moving, removing, and/or exchanging the shield. The method may further include sliding the shield relative to the tubes while the distal portion of the shielding device is inserted to the treatment site.

Example embodiments of the present invention are described in more detail below with reference to the appended Figures.

BRIEF DESCRIPTION OF THE DRAWINGS

FIGS. 2A to 2C show perspective, top and side views of a first exemplary embodiment of a portion of a shielding device according to the present invention.

FIGS. 3A to 3F show top, side, bottom, proximal end, top perspective and bottom perspective views of a first exemplary embodiment of a shield according to the present invention.

FIGS. 4A and 4B show perspective views of different positions of a first exemplary embodiment of the shielding device according to the present invention.

FIGS. 8A and 8B show side and end views of a first exemplary embodiment of a shield depth lock screw of a rotary unit according to the present invention.

FIGS. 9A to 9D show top, side, proximal end and top perspective views of a first exemplary embodiment of the shielding device, rotary unit and assembly block according to the present invention.

FIG. 11 shows a close-up, perspective view of a first exemplary embodiment of a rotary unit and assembly block according to the present invention.

FIG. 13 shows a perspective view of a second exemplary embodiment of a fully assembled assembly including a shielding device according to the present invention.

FIGS. 14A to 14C show top, side and proximal end views of the second exemplary embodiment of a fully assembled assembly including a shielding device according to the present invention.

FIGS. 15A to 15E show perspective, proximal end, top, cross-sectional and side views of a second exemplary embodiment of a shield retainer of a shielding device according to the present invention.

FIGS. 16A to 16D show perspective, proximal end, bottom and side views of a second exemplary embodiment of a shield of a shielding device according to the present invention.

DETAILED DESCRIPTION

Figure 1:
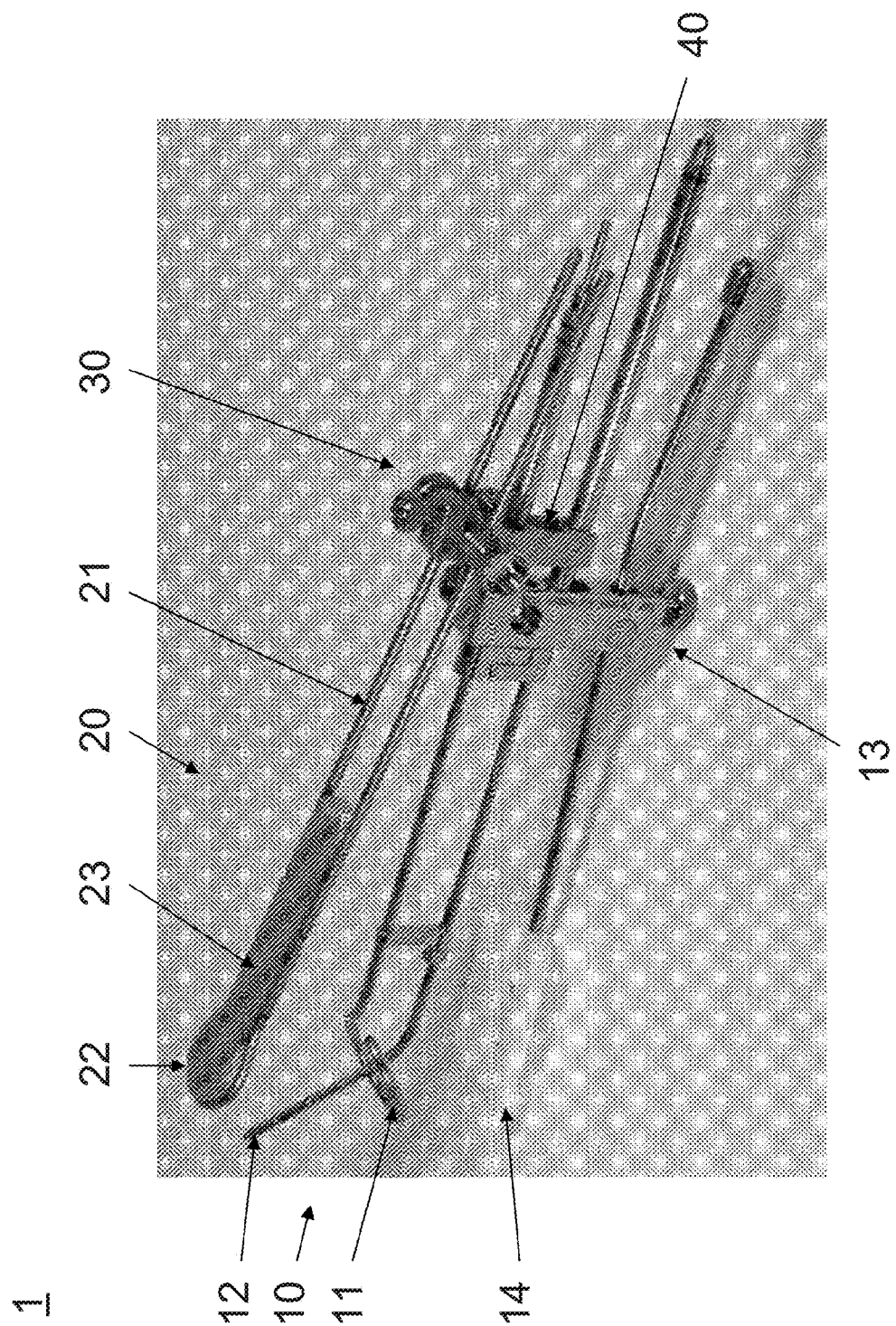
FIG. 1 shows a perspective view of a first exemplary embodiment of an assembly including a shielding device according to the present invention.

FIG. 1 shows a perspective view of a first exemplary embodiment of an assembly 1 including a shielding device 20 according to the present invention.

The assembly 1 may be designed for use with high dose rate ring-tandem applicators 10, high dose rate split ring applicators, or other suitable applicators. Regardless of the specific type of applicator used with the assembly 1, the shielding device 20 provides displacement and/or shielding of healthy organs near the treatment site.

The assembly includes an applicator 10, a shielding device 20, a rotary unit 30, and an assembly block 40. As shown in FIG. 1, the applicator 10 may be a ring-tandem applicator including a ring 11 and a tandem 12 joined to each other at a block 13. Optionally, the applicator 10 may include a rectal retractor 14, also joined at the block 13. Although a particular embodiment of an applicator 10 is shown in the Figures, it is understood that any suitable applicator may be used with the shielding device 20.

FIGS. 2A to 2C show perspective, top and side views of a first exemplary embodiment of a portion of a shielding device 20.

As shown in FIGS. 1 to 2C, the shielding device 20 includes two tubes 21 that extend longitudinally substantially parallel with each other and with the applicator 10. At a distal end of the tubes 21, the shielding device 20 includes a substantially circular and/or U-shaped distal portion 22 that joins the two tubes 21. Alternatively, the distal portion 22 may include other shapes, e.g., oval, polygonal, and others. The tubes 21 and distal portion 22 may extend approximately 9½ inches, and the diameter of the tubes may be approximately ⅛ inch. The proximal ends of the tubes 21 may include spherical buttons (not shown) for safety and/or aesthetics. The tubes 21 and distal portion 22 may be made of medical grade titanium, for example. Further, as shown in FIG. 2C, the distal portion 22 may be angled relative to a plane defined by the two tubes 21 by up to 10 degrees, preferably about 5 degrees.

FIGS. 3A to 3F show top, side, bottom, proximal end, top perspective and bottom perspective views of a first exemplary embodiment of a shield 23. FIGS. 4A and 4B show perspective views of different positions of a first exemplary embodiment of the shielding device 20.

The shield 23 includes a proximal section 24 and a distal section 25. The proximal section 24 and at least a part of the distal section 25 include grooves 26 that allow the shield 23 to be snapped into position between the two tubes 21 and to be slid longitudinally between the two tubes 21, as shown in FIGS. 4A and 4B. The distal section 25 is shaped to correspond to the distal portion 22 of the shielding device 20, which may be substantially circular, for example, as shown in FIGS. 2A to 4B. The shield 23 may be configured to extend at least a length of the distal section 25 along a longitudinal axis of the two tubes 21. Preferably, the shield 23 extends beyond the distal section 25 into the proximal section 24 such that the shield 23 may be reliably secured between the two tubes 21 by grooves 26. The shield 23 may be made of tungsten and/or brass, for example. Further, the shield 23 may be between about 2 mm thick to about 5 mm thick, preferably about 3 mm thick.

When the shield 23 is slid proximally, as shown in FIG. 4A, a position of the shielding device 20 may be more easily confirmed by imaging, e.g., fluoroscopy, CT scanning, and/or MRI. The shield 23 may be slid distally, as shown in FIG. 4B, prior to beginning treatment. Alternatively, the shield 23 may be removed, exchanged, and/or positioned as necessary during all phases of imaging, treatment planning, and actual treatment.

Figure 5:
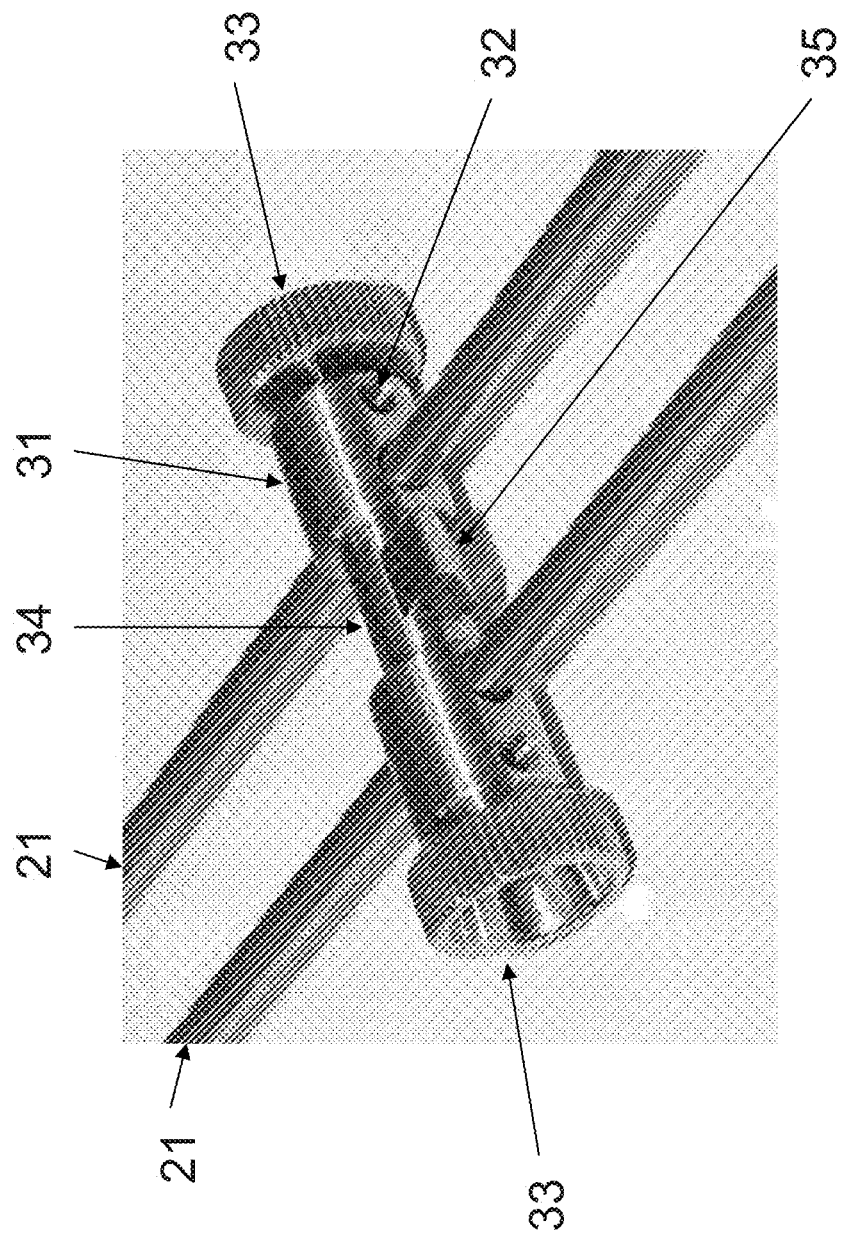
FIG. 5 shows a close-up, perspective view of a first exemplary embodiment of a rotary unit according to the present invention.

FIG. 5 shows a close-up, perspective view of a first exemplary embodiment of a rotary unit 30.

The rotary unit 30 includes shielding device receiving portions 31 having receiving holes 32 and shield depth lock screws 33. The shielding device receiving portions 31 are joined by a bearing portion 34 having a pivot pin 35. The two tubes 21 of the shielding device 20 are received in the holes 32. The tubes 21 may be adjusted longitudinally to a desired insertion depth, and the tubes 21 may be locked in position by rotating the shield depth lock screws 33. The rotary unit 30 may be made of medical grade titanium, for example.

Figure 6C:
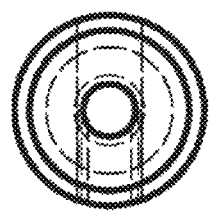
FIGS. 6A to 6C show proximal end, top and side views of a first exemplary embodiment of a portion of a rotary unit according to the present invention.
Figure 6A:
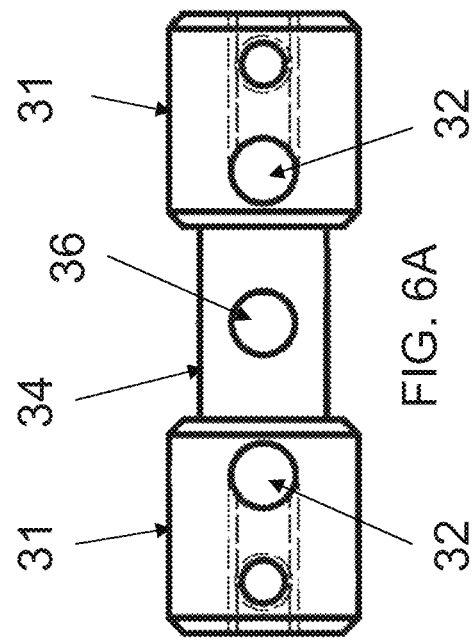
Figure 6B:
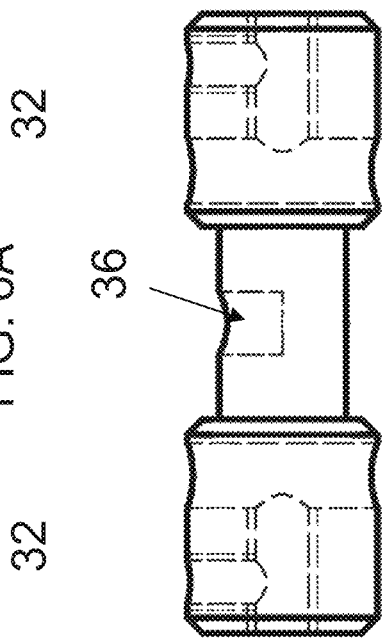
Figure 7C:
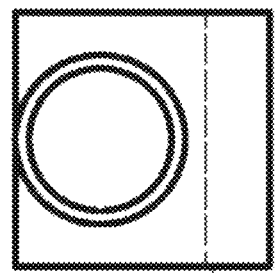
FIGS. 7A to 7C show top, side and distal end views of a first exemplary embodiment of a pivot pin of a rotary unit according to the present invention.
Figures 7A, 7B:
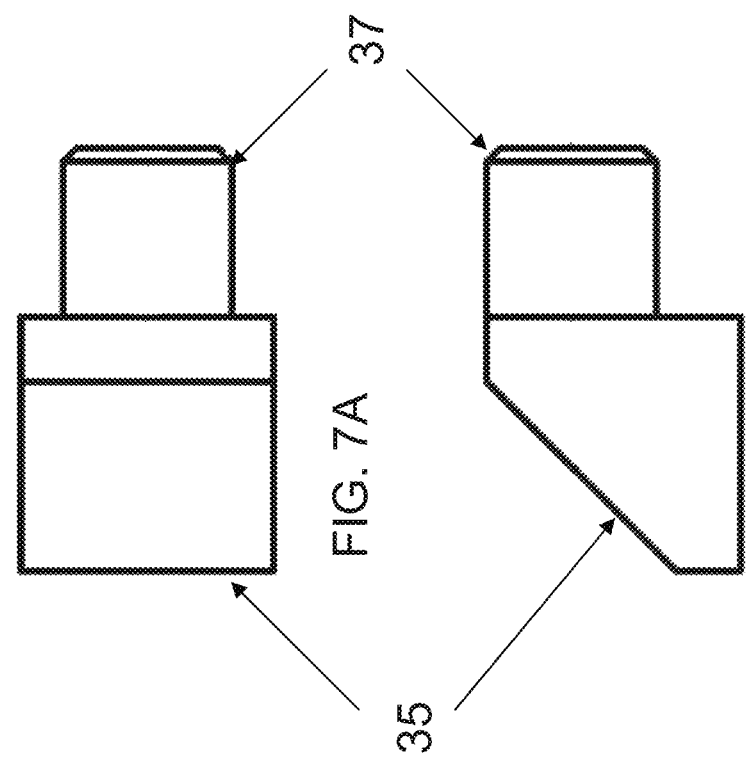
Figure 10D:
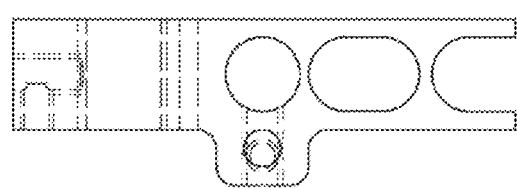
FIGS. 10A to 10D show top, proximal end, side and distal end views of a first exemplary embodiment of a portion of an assembly block according to the present invention.
Figure 10C:
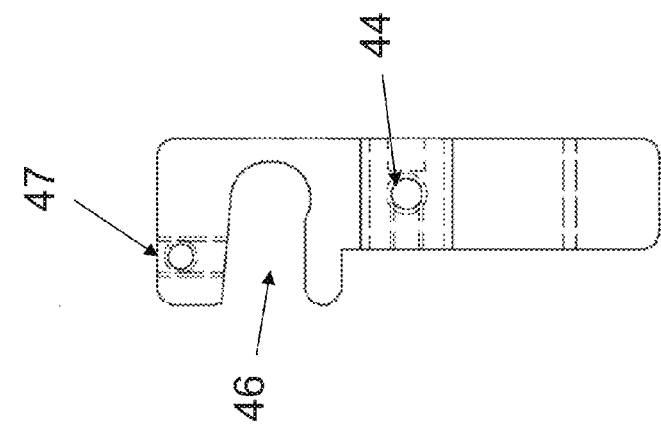
Figure 10A:
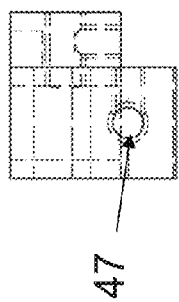
Figure 10B:
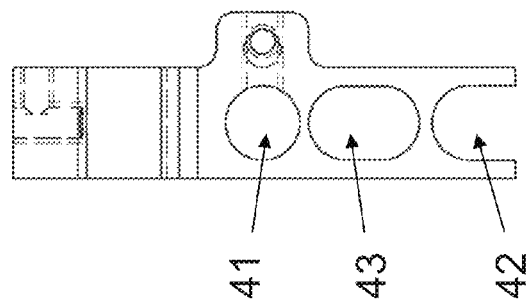

FIGS. 6A to 6C show proximal end, top and side views of a first exemplary embodiment of a portion of a rotary unit 30. FIGS. 7A to 7C show top, side and distal end views of a first exemplary embodiment of a pivot pin 35 of a rotary unit 30. FIGS. 8A and 8B show side and end views of a first exemplary embodiment of a shield depth lock screw 33 of a rotary unit 30.

The rotary unit 30 includes shielding device receiving portions 31 having receiving holes 32. The shielding device receiving portions 31 are joined by a bearing portion 34. The bearing portion 34 includes a pivot pin receiving hole 36, as shown in FIGS. 6A and 6B, in which a pivot pin 35 may be inserted, preferably permanently. The pivot pin 35, as shown in 7A to 7C, includes an inserting pin 37 that is received by pivot pin receiving hole 36. Alternatively, the pivot pin 35 may be formed integrally with bearing portion 34 of rotary unit 30. The pivot pin 35 may be triangular in order to provide a range of angles of the shielding device 20 relative to the applicator 10. Alternatively, other shapes of the pivot pin 35 may be possible, such as for example, rectangular, circular, and/or polygonal, as long as a sufficient range of angles of the shielding device 20 relative to the applicator 10 is possible. The shield depth lock screws 33, as shown in FIGS. 8A and 8B, may be held captive in the rotary unit 30, such that they cannot be completely removed from the rotary unit 30. Further, the screws 33 may have knurled surfaces to facilitate manual operation of the screws 33.

FIGS. 9A to 9D show top, side, proximal end and top perspective views of a first exemplary embodiment of the shielding device 20, rotary unit 30, and assembly block 40. FIGS. 10A to 10D show top, proximal end, side and distal end views of a first exemplary embodiment of a portion of an assembly block 40.

The assembly block 40 is configured to receive the applicator 10 and the rotary unit 30, to which the shielding device 20 is attached. As shown in FIGS. 10A to 10D, the assembly block 40 includes a circular hole 41 and a U-shaped hole 42 configured to received the applicator 10. Further, the assembly block 40 includes an applicator lock screw receiving hole 44 that receives an applicator lock screw, e.g., similar to shield depth lock screw 33, that locks the applicator 10 relative to the assembly block 40. Alternative arrangements, such as for example, elongated holes and/or slots, may be possible to receive and lock the applicator 10 in the assembly block 40. The assembly block 40 may include additional holes 43 for weight reduction. In addition, the assembly block 40 includes a rotary unit receiving portion 46 and an angle adjustment screw hole 47 that receives an angle adjustment screw configured to interact with the rotary unit 30 to set an angle of the shielding device 20 relative to the applicator 10. The assembly block 40 may be made of medical grade titanium, for example.

FIG. 11 shows a close-up, perspective view of a first exemplary embodiment of a rotary unit 30 and assembly block 40.

The applicator 10, including ring 11, tandem 12 and optional rectal retractor 14 held together by block 13, is received in holes 41, 42 of assembly block 40 and locked in place by applicator lock screw 45. In addition, tubes 21 of shielding device 20 are received in rotary unit 30 and locked in place by shield depth lock screws 33. Further, the bearing portion 34 of rotary unit 30 is received in rotary unit receiving portion 46 of assembly block 40. Angle adjustment screw 48 is adjusted to interact with pivot pin 35 of rotary unit 30 to set an angle of shielding device 20 relative to applicator 10. The shielding device 20 is movable within the rotary unit 30 longitudinally along a longitudinal axis of the two tubes 21. Additionally, the shielding device 20 and rotary unit 30 are movable within the assembly block 40 rotationally towards or away from a distal end of the applicator 10.

The assembly 1 including the shielding device 20 is configured to move and/or shield a bladder and/or a rectum during treatment of a patient's cervix. Thus, the shielding device 20 allows for following the principle of radiation protection: time, distance, and shielding. That is, the duration of radiation treatment can be optimally set for the treatment site without compromising the prescription dose, while protecting healthy organs via increased distance and/or shielding from radiation exposure.

Figure 12:
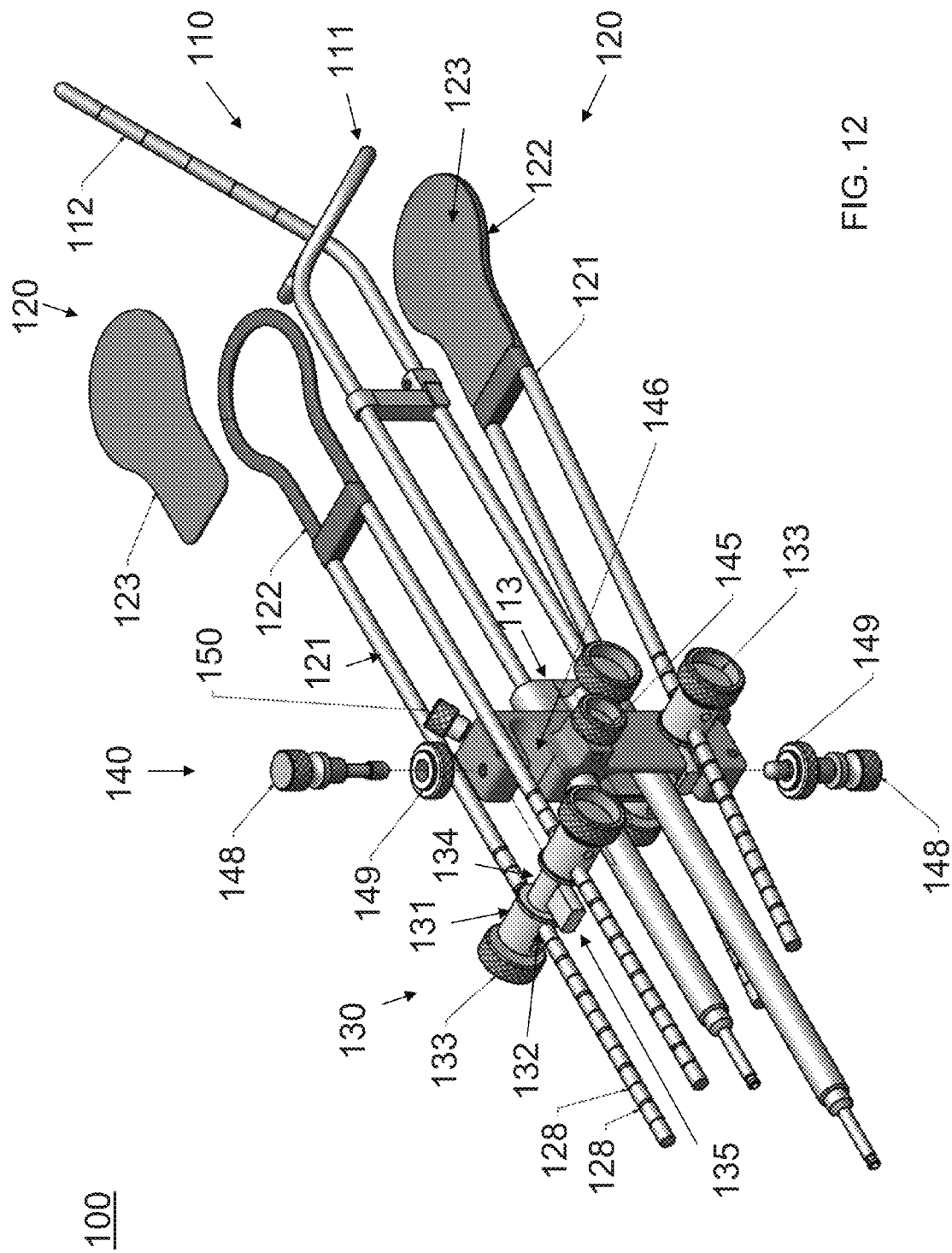
FIG. 12 shows a perspective view of a second exemplary embodiment of a partially assembled assembly including a shielding device according to the present invention.

FIG. 12 shows a perspective view of a second exemplary embodiment of a partially assembled assembly 100 including a shielding device 120. FIG. 13 shows a perspective view of a second exemplary embodiment of a fully assembled assembly 100 including a shielding device 120. FIGS. 14A to 14C show top, side and proximal end views of the second exemplary embodiment of a fully assembled assembly 100 including a shielding device 120.

As shown in the Figures, the assembly 100 includes an applicator 110, two shielding devices 120, two rotary units 130 and an assembly block 140. The applicator 110 includes a ring 111 and tandem 112 joined at a block 113. The assembly 100 may be designed for use with high dose rate ring-tandem applicators 110, high dose rate split ring applicators, or other suitable applicators. Regardless of the specific type of applicator used with the assembly 100, the shielding device 120 provides displacement and/or shielding of healthy organs near the treatment site.

FIGS. 15A to 15E show perspective, proximal end, top, cross-sectional and side views of a second exemplary embodiment of a shield retainer 122 of a shielding device 120. FIGS. 16A to 16D show perspective, proximal end, bottom and side views of a second exemplary embodiment of a shield 123 of a shielding device 120.

Each shielding device 120 includes two tubes 121, a shield retainer 122 at a distal end of the tubes 121, and a shield 123. The shield retainer 122 is substantially circular and/or U-shaped and joins distal ends of the two tubes 121. Alternatively, the shield retainer 122 may include other shapes, e.g., oval, polygonal, and others. The tubes 121 and shield retainer 122 may extend approximately 9½ inches, and the diameter of the tubes may be approximately ⅛ inch. The proximal ends of the tubes 121 may include spherical buttons (not shown) for safety and/or aesthetics. The tubes 121 and shield retainer 122 may be made of medical grade titanium, for example. Further, the shield retainer 122 may be angled relative to a plane defined by the two tubes 121 by up to 10 degrees, preferably about 5 degrees.

The shield 123 may be shaped to correspond to the shield retainer 122 of the shielding device 120. The shield 123 may be made of tungsten and/or brass, for example. Further, the shield 123 may be between about 2 mm thick to about 5 mm thick, preferably about 3 mm thick.

In addition, as shown in FIGS. 15A to 15E, the shield retainer 122 may include a retaining lip 124 and a key slot 125 configured to retain the shield 123. As shown in FIGS. 16A to 16D, the shield 123 may include a retaining ring 126 and a key portion 127 configured to be received by the retaining lip 124 and the key slot 125, respectively, of the shield retainer 122.

When the shield 123 is to be attached to the shield retainer 122, the shield 123 may be rotated and attached to shield retainer 122 such that the retaining ring 126 is inserted within the periphery of the shield retainer 122 and the retaining lip 124 does not abut against retaining ring 126 of shield 123. Then, the shield 123 may be rotated to engage retaining lip 124 with retaining ring 126. Further, when the shield 123 is fully rotated to the assembled position as shown in FIG. 13, for example, the key portion 127 of shield 123 may be received within key slot 125 of shield retainer 122. Thus, the shield 123 may be positively secured within shield retainer 123 to prevent inadvertent disassembly of the shield 123 from the shielding device 120, especially during treatment. The shield 123 may be removed by reversing the order of the steps described above. The shield 123 may be removed, exchanged, and/or positioned as necessary during all phases of imaging, treatment planning, and actual treatment.

As shown in FIGS. 12 to 14C, each rotary unit 130 includes shielding device receiving portions 131 having receiving holes 132 and shield depth lock screws 133. The shielding device receiving portions 131 are joined by a bearing portion 134 having a pivot pin 135. The tubes 121 of each shielding device 120 are received and longitudinally situated within receiving holes 132 of a respective rotary unit 130. The tubes 121 may be adjusted longitudinally to a desired insertion depth, and the tubes 121 may be locked in position by rotating the shield depth lock screws 133. The tubes 121 may further include markings and/or grooves 128 that indicate a depth of insertion of the shielding device 120. For example, the markings 128 may be placed every 5 mm and/or 1 cm, or any other length, along the tubes 121. In addition, the markings 128 may be the same or different from each other. By the use of such markings 128, a longitudinal position of the shielding device 120 may be set such that the shielding device 120 may be reproducibly inserted to a desired depth. The rotary unit 130 may be made of medical grade titanium, for example.

The pivot pin 135 may be triangular in order to provide a range of angles of the shielding device 120 relative to the applicator 110. Alternatively, other shapes of the pivot pin 135 may be possible, such as for example, rectangular, circular, and/or polygonal, as long as a sufficient range of angles of the shielding device 120 relative to the applicator 110 is possible. The shield depth lock screws 133 may be held captive in the rotary unit 130, such that they cannot be completely removed from the rotary unit 130. Further, the screws 133 may have knurled surfaces to facilitate manual operation of the screws 133.

The assembly block 140 receives ring 111 and tandem 112 of applicator 110 in holes 141, 142 of assembly block 140, and the applicator lock screw 145 secures the applicator 110 in place. The assembly block 140 may be made of medical grade titanium, for example.

In addition, the bearing portion 134 of each rotary unit 130 is received in a rotary unit receiving portion 146 of assembly block 140. After insertion, the bearing portion 134 may be retained, while maintaining rotational freedom, by a capture screw 150. The angle of the rotary unit 130 may be adjusted by inserting, into angle adjustment screw hole 147, an angle adjustment screw 148 that interacts with the pivot pin 135 of the rotary unit 130. Further, an angle location lock nut 149 may be provided on angle adjustment screw 148 to reproducibly set a rotational position of rotary unit 130. That is, when the angle adjustment screw 148 is inserted to a desired depth, the angle location lock nut 149 may be turned to abut against assembly block 140, thereby setting an insertion depth of screw 148. Thereafter, screw 148 can be removed and reproducibly reinserted to the desired depth, thereby setting the desired rotational position of rotary unit 130 and the attached shielding device 120. Accordingly, the shielding device 120 is movable within the rotary unit 130 and can be set to a reproducible longitudinal position along a longitudinal axis of the two tubes 121. Additionally, the shielding device 120 and rotary unit 130 are movable within the assembly block 140 and can be set to a reproducible rotational position with respect to a distal end of the applicator 110.

The assembly 100 including the shielding device 120 is configured to move and/or shield a bladder and/or a rectum during treatment of a patient's cervix. Further, as shown in FIGS. 12 to 14C, by the provision of a shielding device 120 on opposite sides of the applicator 110, one shielding device may shield the bladder and the other shielding device may simultaneously shield the rectum during radiation treatment of a patient's cervix. Thus, the shielding device 120 allows for following the principle of radiation protection: time, distance, and shielding. That is, the duration of radiation treatment can be optimally set for the treatment site without compromising the prescription dose, while protecting healthy organs via increased distance and shielding from radiation exposure.

Figure 17:
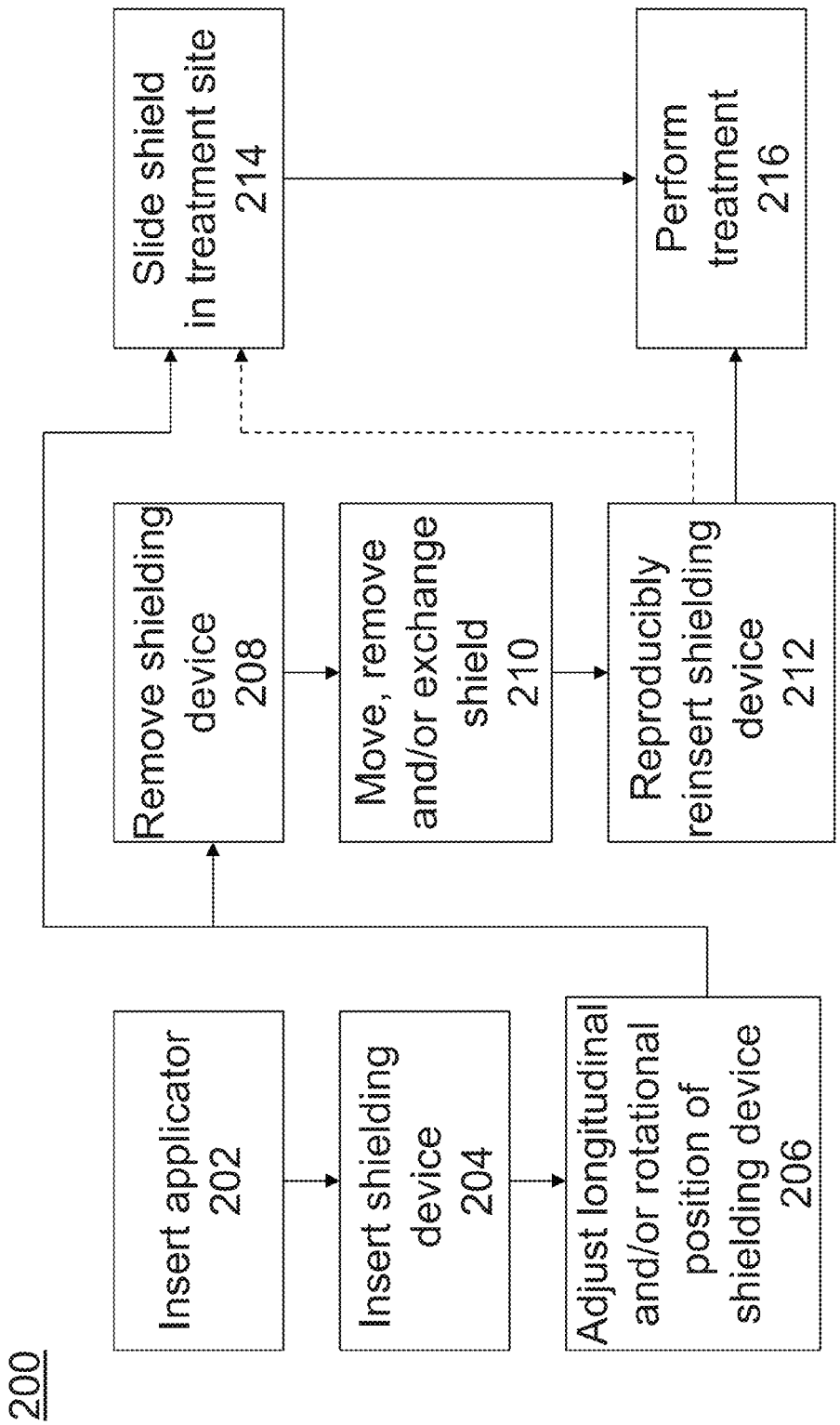
FIG. 17 schematically shows a method of using an exemplary embodiment of a shielding device according to the present invention.

FIG. 17 schematically shows a method 200 of using an exemplary embodiment of a shielding device.

At step 202, a distal end of an applicator may be inserted to a treatment site. At step 204, a distal portion of the shielding device is inserted to the treatment site, and at step 206, a position of the distal portion is adjusted relative to a distal end of the applicator. The adjustment may include longitudinal and/or rotational adjustment of the shielding device relative to the applicator. That is, a longitudinal depth of insertion of the shielding device may be adjusted and/or reproducibly set, for example, by moving the tubes 21, 121 based on markings 128 and thereafter locking the tubes by shield depth lock screws 33, 133; a rotational position of the shielding device may be adjusted and/or reproducibly set, for example, by rotating the shielding device and rotary unit using pivot pin 35, 135, angle adjustment screw 48, 148 and angle location lock nut 149. After the adjustment at step 206, the distal portion of the shielding device may be removed from the treatment site at step 208. The shield may be moved, removed, and/or exchanged at step 210. Then, at step 212, the distal portion of the shielding device may be reproducibly reinserted to the previously adjusted position, i.e., the previously adjusted and/or set longitudinal and rotational positions. Alternatively or additionally, at step 214, the shield may be slid relative to the two tubes while the distal portion of the shielding device remains inserted to the treatment site. Finally, at step 216, radiation treatment may be performed.

At any point in the above-described method 200, imaging, e.g., fluoroscopy, CT scanning and/or MRI, may be performed to determine the position of the shielding device and/or the assembly relative to the treatment site. For example, to facilitate imaging of the position of the shielding device, the shielding device may initially have no shield or a shield of different material, e.g., plastic, that does not interfere with imaging. After adjustment of the position of the shielding device, the shield may be added or, in the case of a plastic shield, exchanged, prior to beginning radiation treatment. Optionally, the shielding device may be used without a shield during radiation treatment, such that the shielding device then serves primarily to move the bladder and/or rectum during treatment.

Although the present invention has been described with reference to particular examples and exemplary embodiments, it should be understood that the foregoing description is in no manner limiting. Moreover, the features described herein may be used in any combination.

What is claimed is:

1. A shielding device, comprising:
   two elongated, parallel tubes joined at a distal portion of the tubes; and
   a shield at least one of removably and slidably situated at the distal portion;
   wherein the distal portion includes a separate shield retainer attached to distal ends of the tubes; and wherein the shield retainer includes a retaining lip and a key slot configured to retain the shield, and the shield includes a retaining ring and a key portion configured to be received by the retaining lip and the key slot, respectively.

2. The shielding device according to claim 1, wherein the distal portion is angled up to about 10 degrees relative to a plane defined by the tubes.

3. The shielding device according to claim 1, wherein the tubes include markings configured to indicate a longitudinal position.

4. The shielding device according to claim 1, wherein the tubes are made of medical grade titanium.

5. The shielding device according to claim 1, wherein the shield is made of tungsten and/or brass.

6. The shielding device according to claim 1, wherein the shield is between about 2 mm and about 5 mm thick.

7. The shielding device according to claim 1, wherein the shield is configured to extend at least a length of the distal portion along a longitudinal axis of the tubes.

8. The shielding device according to claim 1, wherein the shielding device is configured to be attached to an applicator via a rotary unit and an assembly block.

9. The shielding device according to claim 8, wherein the shielding device is movable within the rotary unit and the assembly block longitudinally along a longitudinal axis of the tubes and/or rotationally towards or away from a distal end of the applicator.

10. The shielding device according to claim 1, wherein the shielding device is configured to move and/or shield a bladder and/or a rectum during treatment of a patient's cervix.

11. An assembly, comprising:
   an applicator configured for a treatment site;
   an assembly block attached to the applicator;
   at least one rotary unit configured to be rotatably received in the assembly block; and
   at least one shielding device, each shielding device including:
      two elongated, parallel tubes joined at a distal portion; and
      a shield at least one of removably and slidably situated at the distal portion;
   wherein the tubes of each shielding device are configured to be movably received in a respective rotary unit,
   wherein the rotary unit includes a pivot pin, and the assembly block includes at least one angle adjustment screw configured to interact with the pivot pin, the pivot pin and the angle adjustment screw configured to set a rotational position of the rotary unit when received in the assembly block; and
   wherein the pivot pin is triangular and/or rectangular.

12. The assembly according to claim 11, wherein the assembly, except for the shield, is made of medical grade titanium.

13. The assembly according to claim 11, wherein the assembly block is attached to the applicator via an applicator lock screw.

14. The assembly according to claim 11, wherein the assembly block includes a circular hole, an elongated hole, and/or a U-shaped hole adapted to receive the applicator.

15. The assembly according to claim 11, wherein the rotary unit is rotatably retained in the assembly block via a capture screw.

16. The assembly according to claim 11, wherein the tubes are secured in the rotary unit via shield depth lock screws.

17. The assembly according to claim 11, wherein the at least one angle adjustment screw includes an angle location lock nut configured to reproducibly set the rotational position.

18. The assembly according to claim 11, wherein the shielding device is configured to move and/or shield a bladder and/or a rectum during treatment of a patient's cervix.

\* \* \* \* \*